United States Patent
Snyder

(10) Patent No.: US 7,589,183 B2
(45) Date of Patent: Sep. 15, 2009

(54) PREVENTION OF LEACHING OF LIGANDS FROM AFFINITY-BASED PURIFICATION SYSTEMS

(75) Inventor: Mark A. Snyder, Oakland, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 25 days.

(21) Appl. No.: 11/563,961

(22) Filed: Nov. 28, 2006

(65) Prior Publication Data

US 2008/0124812 A1    May 29, 2008

(51) Int. Cl.
*C07K 14/00* (2006.01)
*G01N 30/02* (2006.01)

(52) U.S. Cl. ...................... 530/413; 436/161
(58) Field of Classification Search .............. None
See application file for complete search history.

(56) References Cited

U.S. PATENT DOCUMENTS 4,983,722 A * 1/1991 Bloom et al. ............ 530/387.1
5,429,746 A * 7/1995 Shadle et al. ............... 210/635
7,385,040 B2   6/2008 Johansson et al.

OTHER PUBLICATIONS

Bloom et al., "Detection and reduction of protein A contamination in immobilized protein A purified monoclonal antibody preparations", J Immunol Methods 117(1): 83-89 (Feb. 8, 1989). (Abstract Only).*

* cited by examiner

*Primary Examiner*—Anand U Desai
(74) *Attorney, Agent, or Firm*—Townsend and Townsend and Crew LLP.; M. Henry Heines

(57) ABSTRACT

In an affinity-type purification, ligands dissociated from the stationary phase that would otherwise leach into the species being purified are captured by a second ligand that is also incorporated into the stationary phase, the second ligand exhibiting an affinity-type interaction with the dissociated first ligand with sufficient specificity to avoid the undesired retention by the second ligand of species from the liquid sample or source liquid other than the species sought to be purified in the affinity column.

10 Claims, No Drawings

PREVENTION OF LEACHING OF LIGANDS FROM AFFINITY-BASED PURIFICATION SYSTEMS

BACKGROUND OF THE INVENTION

1. Field of the Invention

This invention resides in the field of affinity chromatography, and addresses concerns arising from the labile character of ligands coupled to a support as the stationary phase.

2. Description of the Prior Art

Affinity chromatography is widely used for separating and detecting components in biological samples and for the isolation or purification of biological species or recombinant species from clinical samples, from cell growth cultures, or from any medium in which the species are produced or can be extracted. Affinity chromatography is commonly performed by passing a liquid medium containing the species of interest through a column or membrane to which a ligand is bound as a stationary phase, the ligand being one to which the species of interest binds by an affinity-type interaction. Affinity chromatography that is used to isolate and purify species is also termed "affinity extraction," and the species-ligand interaction in this type of extraction is one that occurs with sufficient specificity to differentiate between the species of interest and other species in the source liquid. Affinity extraction techniques include immunoextraction in which the ligands are antibodies; protein-protein extractions using such ligands as wheat germ agglutinin, concanavalin A, protein A, and protein G; and interactions involving non-protein species such as heparin or nucleic acids. Once immobilized on the solid phase by the affinity interaction, the species of interest is removed from the solid phase by an appropriate change in conditions such as a change in pH or the introduction of a detergent, chaotrope, salt, competitive binding species, or any agent that will overcome or lessen the binding affinity of the species to the solid phase. The types of changes that will be effective in releasing the bound species in particular systems are well known in the art of affinity chromatography.

The ligand is typically a protein or other affinity-binding species that is coupled to a solid support by covalent bonds, the support often having been activated to facilitate the formation of such bonds. Activation commonly involves the placement of a reactive group, such as for example an epoxide group, on the support surface. The linkage between the ligand and the support is labile, however, often resulting in dissociation of the ligand from the support during the passage of liquids through the medium. In addition, leaching can occur by enzymatic or chemical degradation of the ligand itself, such as proteolysis of protein affinity ligands by proteases in the process stream, cleavage of nucleic acids by endo- and exo-nucleases in the process stream, etc. The affinity ligand that is leached from the affinity medium as a result of this dissociation may be small compared to the amount of ligand remaining on the support, but even a small amount of leached ligand can seriously contaminate the otherwise purified species eluted from the medium. When a therapeutic agent that is either biologically derived or produced by recombinant chemistry is contaminated with a leached affinity ligand, the leached ligand can recombine with the agent and thereby impede the effectiveness of the agent, or combine with, or impede the functions of, other species such as membranes, cell walls, or enzymes in the patient's body to cause harm. Concavalin A, for example, is an affinity ligand that is used for purifying lysosomal enzyme preparations, but is known to leach from affinity columns and contaminate the enzyme preparations, particularly by activating T cells in the patient to whom the enzyme preparation is administered. To eliminate these types of contamination, the leached ligands must be removed, and this is typically performed by separations downstream of the affinity column or membrane. This adds cost and time to the preparation.

SUMMARY OF THE INVENTION

The present invention resides in an affinity medium, method, and system that prevents species purified in the medium from being contaminated with leached proteins from the medium or leached segments of the proteins that have become dissociated during the passage of liquids through the medium. This is achieved by a stationary phase that contains at least two ligands immobilized on a support. The first ligand is the ligand that binds to the solute, i.e., the species to be purified, and the second ligand is one that binds selectively to molecules of the first ligand or dissociated segments thereof that are not, or are no longer, immobilized on the support. Both ligands bind to their respective binding partners by an affinity-type interaction. Thus, while the affinity-binding proteins are initially immobilized on the stationary phase by covalent binding, leached molecules of these proteins are captured by affinity binding in the same separation medium, whether the medium be a column, a membrane, or any other form of stationary phase. A single affinity medium therefore serves both to isolate the species of interest and to remove contaminants that would otherwise arise within the affinity medium itself.

These and other features, advantages, and objects of the invention will be apparent from the description that follows.

DETAILED DESCRIPTION OF THE INVENTION AND PREFERRED EMBODIMENTS

Ligands used as the stationary phase in the practice of this invention are referred to herein as the "first ligand" to differentiate these ligands from the "second ligand" which represents ligands used to capture leached molecules of the first ligand. The first ligand includes any of the wide variety of ligands that are used in affinity chromatography, and preferably those that are disclosed in the literature or used in clinical laboratories, research laboratories, or production facilities, as stationary phases for affinity extraction. First ligands can be protein ligands, polysaccharides, or other large molecules that engage in affinity binding. Lectins are examples of ligands useful as the first ligand, effective for extracting certain types of carbohydrates, such as polysaccharides, glycoproteins, and glycolipids. Specific lectins include concavalin A, wheat germ agglutinin, jacalin, and lectins found in peas, peanuts, and soybeans. Protein A and protein G, useful in binding to the constant regions of many types of immunoglobulins, are further examples of ligands useful as the first ligand. A ligand demonstrating the binding behavior of both protein A and G is the recombinant protein known as protein A/G, which is also useful as the first ligand. In immunoextraction, as noted above, the first ligand is an antibody (including monoclonal antibodies) or an antibody fragment. Examples of species purified by immunoextraction using these ligands are anti-idiotypic antibodies, glucosaccharides, granulocyte colony-stimulating factor, human serum albumin, IgG, IgE, interferon, tumor necrosis factor, interleukins, recombinant Factor VIII, and transferrin. Still further examples of the first ligand are non-protein ligands. Examples of these are aptamers and heparin. Aptamers exhibit antibody-type interactions and are known for affinity-type binding to adenosine and for chiral separations, while heparin is useful for purifying certain lipoproteins.

The support for the stationary phase can be of any material and configuration that are known to be functional in affinity chromatography. Examples are particles and beads, which can be packed, fluidized, or immobilized. Other examples are fibers, foams, frits, microporous films, membranes and substrates with microreplicated surfaces. When a microporous film is used, it can be attached to the inner surface of a capillary, a well in a multi-well plate, or a reaction vessel, as a lining on the surface. When particles or beads are used, they can be rigid solids or semi-solids such as gels.

The second ligand, which captures dissociated molecules of the first ligand to prevent these molecules from leaching into the product, is chosen for its affinity binding specificity toward the first ligand, and the choice will therefore be governed or dictated by the first ligand. Examples of species suitable for use as the second ligand thus include monoclonal antibodies, proteins, small peptides, aptamers, and organic species such as triazines and boronates. The second ligand will be selected as one that does not bind other species in the liquid mixture that contains the species of interest and thereby does not significantly change the purity of the final product by virtue of retaining extraneous species in the affinity medium, other than molecules of the first ligand that have become dissociated and would otherwise leach out of the medium.

The first and second ligand can be coupled to the support by conventional coupling chemistries, typically using activated or functionalized supports, such as for example epoxide-functionalized supports. Examples of the types of linkage are ether linkages, thiol linkages, amino linkages, carboxyl linkages, and aldehyde linkages. When the stationary phase is a non-moving phase, such as a packed bed, membrane, or surface, the first and second ligands can be uniformly distributed throughout the phase, or they can be fully or partially segregated, such as for example with the second ligand concentrated at sites downstream from the first ligand in the direction of the flow of the liquid through or across the stationary phase. A uniform distribution of both ligands throughout the stationary phase is preferred. When the stationary phase is in the form of particles or beads, the two ligands can be coupled to separate populations of particles or beads and the two populations then mixed together, or the two ligands can be coupled to the same particles or beads, such that certain particles or beads contain both types of ligand.

The relative amounts of first and second ligand can be selected on the basis of known or suspected dissociation rates of the first ligand, and may vary with the first ligand and the type of linkage joining the first ligand to the support. In most cases, however, best results will be achieved when the molar percentage of second ligand relative to first ligand is from about 0.01% to about 30%, and preferably from about 0.3% to about 10%. In terms of the weight percent of the ligands relative to a resin that serves as the support, the amount of first ligand will often be from about 0.3 g to about 30 g of ligand per liter of resin, or more often from about 1 g to about 10 g per liter of resin, and the amount of second ligand will often be from about 0.001 g to about 10 g per liter of support, or preferably from about 0.003 g to about 3 g per liter of support.

A source liquid containing a solute of interest can be placed in contact with an affinity medium meeting the above description for purposes of purification in the same manner that such liquids are contacted with affinity media of the prior art. The medium can thus be retained in a flow-through column and a source liquid passed through the column, or the medium can be suspended in the source liquid, incubated sufficiently to allow the binding to occur, and the solid and liquid phases then separated. In either case, the contact between the source liquid and the affinity medium is performed under conditions that will allow the solute to bind to the affinity medium. Such conditions are likewise known in the art, and involve such parameters as the pH, ionic strength, contact time, and the presence or absence of other components in the liquid phase. Once binding has occurred, the unbound components are washed from the medium, using conventional washing media that will not cause dissociation of the solute of interest. Once the washing is complete, the solute is dissociated from the medium and collected by exposing the medium to the dissociation conditions most appropriate to the species involved. As noted above, the dissociation conditions may be a change in pH or the introduction of a detergent, a chaotrope, a salt, or competitive binding species. The result will be a solution of the solute that is purified relative to other solutes in the source liquid. The expression "purified relative" is used herein to mean that while the concentration of the solute of interest as recovered from the affinity medium may be the same, greater than, or less than its concentration in the source solution, other solutes originally present in the source solution will be either significantly reduced in concentration, reduced to concentrations below the level of detection, or eliminated entirely.

The terms "a" or "an" as used in the appended claims are intended to mean "one or more." The term "comprise," and variations thereof such as "comprises" and "comprising," when preceding the recitation of a step or an element is intended to mean that the addition of further steps or elements is optional and not excluded. All patents, patent applications, and other published reference materials cited in this specification are hereby incorporated herein by reference in their entirety. Any discrepancy between any reference material cited herein and an explicit teaching of this specification is intended to be resolved in favor of the teaching in this specification. This includes any discrepancy between an art-understood definition of a word or phrase and a definition explicitly stated in this specification of the same word or phrase.

The foregoing is offered primary for purposes of illustration. Further variations and substitutions that likewise utilize the fundamental features of novelty and utility described herein will be apparent to those skilled in the art and are likewise encompassed by the scope of the claims.

What is claimed is:

1. An affinity medium for extracting a solute from a liquid sample, said affinity medium comprising first and second ligands immobilized on common beads of a packed bed of solid beads, said first ligand binding selectively to said solute by affinity-type binding, and said second ligand binding selectively by affinity-type binding to molecules of said first ligand or to segments of said molecules upon release of said molecules or segments from said solid beads.

2. The affinity medium of claim 1 wherein said first and second ligands are both immobilized on said solid beads by covalent binding to said solid beads.

3. The affinity medium of claim 1 wherein said first ligand is a member selected from the group consisting of a lectin, heparin, protein A, and protein G.

4. The affinity medium of claim 1 wherein said second ligand is a member selected from the group consisting of a monoclonal antibody, an aptamer, a triazine, and a boronate.

5. The affinity medium of claim 1 wherein said second ligand is present on said medium in a quantity equal to 0.01% and about 30% of said first ligand, on a molar basis.

6. The affinity medium of claim 1 wherein said second ligand is present on said medium in a quantity equal to 0.3% and about 10% of said first ligand, on a molar basis.

7. A process for extracting a solute from a liquid sample, said process comprising (a) contacting said liquid sample with an affinity medium in accordance with claim 1, under conditions causing said solute to bind to said first ligand,
(b) washing said affinity medium of said sample while said solute is so bound, and
(c) dissociating said solute from said affinity medium in a purified form relative to other solutes in said sample.

8. The process of claim 7 wherein said first and second ligands are both immobilized on said solid beads by covalent binding to said solid beads.

9. The process of claim 7 said first ligand is a member selected from the group consisting of a lectin, heparin, protein A, and protein G.

10. The process of claim 7 wherein said second ligand is a member selected from the group consisting of a monoclonal antibody, an aptamer, a triazine, and a boronate.

\* \* \* \* \*